United States Patent
Mikoshiba et al.

(10) Patent No.: US 7,183,422 B2
(45) Date of Patent: Feb. 27, 2007

(54) OXONOL COMPOUND AND PROCESS FOR PRODUCING THE COMPOUND

(75) Inventors: Hisashi Mikoshiba, Kanagawa (JP); Masaharu Akiba, Minami-Ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/559,392

(22) PCT Filed: May 26, 2005

(86) PCT No.: PCT/JP2005/010097

§ 371 (c)(1),
(2), (4) Date: Dec. 6, 2005

(87) PCT Pub. No.: WO2005/116119

PCT Pub. Date: Aug. 12, 2005

(65) Prior Publication Data

US 2006/0142597 A1    Jun. 29, 2006

(30) Foreign Application Priority Data

May 28, 2004    (JP)    ............................. 2004-158997

(51) Int. Cl.
*C07D 319/06*    (2006.01)
*C07D 319/08*    (2006.01)

(52) U.S. Cl. ...................................... 549/274; 549/333
(58) Field of Classification Search ................ 549/274, 549/333

See application file for complete search history.

(56) References Cited

FOREIGN PATENT DOCUMENTS

| JP | 2000-52658 A | 2/2000 |
|---|---|---|
| JP | 2001-146074 A | 5/2001 |
| JP | 2003-39830 A | 2/2003 |
| JP | 2004-188968 A | 7/2004 |

OTHER PUBLICATIONS

P. Safer, "Dichotomy in the ring opening reaction of 5-[(2-furyl)methylidene]-2,2-dimethyl-1,3-dioxane-4,6-dione with cyclic secondary amines", Collection of Czechoslovak Chemical Communications, 2000, pp. 1911-1938, vol. 65, No. 12.
Hans-Martin Weber, et al., "Azahexamethin-Neutrocyanine mit einem Disminocyclopropenyliden-Auxochrom", Chemische Berichte, 1988, pp. 1791-1794, vol. 121, No. 10.
International Search Report dated Jul. 12, 2005.

*Primary Examiner*—Bernard Dentz
(74) *Attorney, Agent, or Firm*—Sughrue Mion, PLLC

(57) ABSTRACT

A compound represented by the formula (I) defined herein and a compound represented by the formula (II) defined herein, and a process for producing the compound represented by the formula (I) which comprises reacting the compound represented by the formula (III) defined herein with the compound represented by the formula (IV) defined herein.

10 Claims, No Drawings

OXONOL COMPOUND AND PROCESS FOR PRODUCING THE COMPOUND

This application is a national stage entry of PCT/JP05/10097 filed May 26, 2005.

1. Technical Field

The present invention relates to a compound useful as an intermediate for an oxonol dye and to a process for producing the compound. More particularly, the invention relates to a compound useful as an intermediate for an oxonol dye for use in heat mode type information-recording media in which information is recorded with a visible laser light, which are represented by recordable digital versatile disks (DVD-R's), and to a process for producing the compound.

2. Background Art

Information-recording media (optical disks) in which information recording with a laser light is possible only once have been known. This kind of information-recording medium, which is also called a recordable CD (so-called CD-R), has an advantage that a small quantity of such CD's can be rapidly provided at a reasonable price as compared with the production of conventional CD's. The demand for such CD's is increasing with the recent spread of personal computers. The typical structure of CD-R type information-recording media comprises a transparent disk substrate and, superposed thereon in the following order, a recording layer comprising an organic dye, a reflecting layer comprising a metal, e.g., gold, and a protective layer made of a resin.

Information recording in such an optical disk is accomplished by irradiating the disk with a laser light in the near infrared region (usually a laser light having a wavelength around 780 nm) to locally heat and deform the recording layer. On the other hand, information reading (reproduction) is generally conducted by irradiating the disk with a laser light having the same wavelength as the laser light used for recording to thereby detect a difference in reflectance between those areas in the recording layer which have been thermally deformed (recorded areas) and the areas which have not been deformed (unrecorded areas).

Recently, there is a desire for an information-recording medium having a higher recording density. For heightening recording density, it is effective to reduce the diameter of the laser beam with which the recording medium is irradiated. It is known that laser lights having shorter wavelengths are theoretically advantageous for density increase because the shorter the wavelength of a laser light, the more the laser beam can be narrowed. Consequently, an optical disk capable of recording/reproducing with a laser light having a wavelength shorter than 780 nm, which has been used hitherto, is being developed. For example, an optical disk called a recordable digital video disk (so-called DVD-R) is on the market. This optical disk is produced by forming a recording layer comprising a dye on a transparent disk substrate having a diameter of 120 mm or 80 mm and having a pre-groove with a track pitch of 0.8 μm, which is narrower than 1.6 μm for CD-R's, generally further forming a reflecting layer and a protective layer on the recording layer, and bonding the resultant disk to the same disk or to a disk-form protective substrate of the same size as the disk by means of an adhesive, with the recording layer faced inward. In the DVD-R, recording and reproduction are conducted based on irradiation with a visible laser light (usually a laser light having a wavelength in the range of 600–700 nm) and higher-density recording than in CD-R type optical disks is possible.

JP-A-63-209995 discloses a CD-R type information-recording medium having, formed on a substrate, a recording layer comprising an oxonol dye. There is a description therein to the effect that use of that dye compound enables recording/reproducing characteristics to be stably maintained overlong. The oxonol dye compound described therein is one having an ammonium in a salt form incorporated in the molecule. On the other hand, JP-A-2000-52658 describes an oxonol dye compound which shows high light resistance and durability and provides an optical information-recording medium having satisfactory recording characteristics.

General oxonol dye moieties can be synthesized by the condensation reaction of the corresponding active methylene compound with a methine source (a compound used for incorporating one or more methine groups in methine dye synthesis). This kind of dye is described in detail in JP-B-39-22069, JP-B-43-3504, JP-B-52-38056, JP-B-54-38129, JP-B-55-10059, JP-B-58-35544, JP-A-49-99620, JP-A-52-92716, JP-A-59-16834, JP-A-63-316853 (U.S. Pat. No. 4,920,031), JP-A-64-40827, British Patent 1,133,986, U.S. Pat. No. 3,247,127, U.S. Pat. No. 4,042,397, U.S. Pat. No. 4,181,225, U.S. Pat. No. 5,213,956, U.S. Pat. No. 5,260,179, International Publication No. 02/080161, JP-A-63-209995 and JP-A-2-62279.

Although a compound having a specific structure is described in "Collection of Czechoslovak Chemical Communications, 1911–1938, 65, 12, 2000", this prior-art technique has no relation with the present invention.

DISCLOSURE OF THE INVENTION

The present inventors made investigations on methods of synthesizing oxonol dye compounds. As a result, it has been found that the compound of the invention is a useful intermediate for an oxonol dye which is a preferred dye for use in DVD-R's. The invention has been completed based on this finding. The compound of the invention is especially useful for synthesizing an oxonol dye obtained by dimerization in which two chromophores are bonded through a connecting group by covalent bonding.

An object of the invention is to provide a compound from which an oxonol dye retaining satisfactory recording characteristics and realizing a high reflectance and a high degree of modulation even in high-speed recording at a 4-fold speed or higher can be synthesized. This dye has a complex refractive index in which the real part n is large and the imaginary part k is almost the same or small. Furthermore, the oxonol dye derived from the compound of the invention attains a sufficiently low jitter in a wide range of recording speeds of from 1- to 16-fold speeds.

The object of the invention can be advantageously accomplished with the constitutions described below.

(1) A Compound Represented by the Following Formula (I):

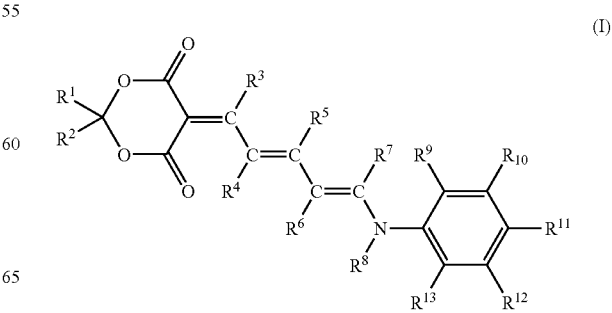

wherein $R^1$ and $R^2$ each independently represent a hydrogen atom, a substituted or unsubstituted alkyl group having 1–10 carbon atoms, or a substituted or unsubstituted aryl group having 6–10 carbon atoms; $R^3$, $R^4$, $R^6$, and $R^7$ each independently represent a hydrogen atom or a substituted or unsubstituted alkyl group having 1–10 carbon atoms; $R^5$ represents a hydrogen atom, a halogen atom, a substituted or unsubstituted alkyl group having 1–10 carbon atoms, a substituted or unsubstituted aryl group having 6–10 carbon atoms, a substituted or unsubstituted acylamino group having 2–10 carbon atoms, or a substituted or unsubstituted heterocyclic group having 1–6 carbon atoms; $R^8$ represents a hydrogen atom or a substituted or unsubstituted acyl group having 2–10 carbon atoms; and $R^9$, $R^{10}$, $R^{11}$, $R^{12}$, and $R^{13}$ each independently represent a hydrogen atom or a substituent; provided that substituents $R^1$ and $R^2$ maybe bonded to each other to form a ring (preferably a 6-membered ring, e.g., cyclohexane).

(2) A Compound Represented by the Following Formula (II):

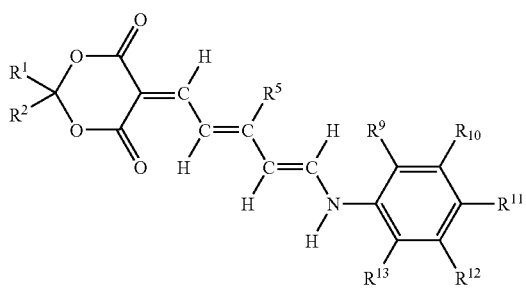

wherein $R^1$ and $R^2$ each independently represent a hydrogen atom, a substituted or unsubstituted alkyl group having 1–10 carbon atoms, or a substituted or unsubstituted aryl group having 6–10 carbon atoms; $R^5$ represents a hydrogen atom, a halogen atom, a substituted or unsubstituted alkyl group having 1–10 carbon atoms, a substituted or unsubstituted aryl group having 6–10 carbon atoms, a substituted or unsubstituted acylamino group having 2–10 carbon atoms, or a substituted or unsubstituted heterocyclic group having 1–6 carbon atoms; and $R^9$, $R^{10}$, $R^{11}$, $R^{12}$, and $R^{13}$ each independently represent a hydrogen atom, a halogen atom, an alkyl group, a cyano group, a nitro group, a carboxyl group, a substituted or unsubstituted alkoxy group having 1–10 carbon atoms, a substituted or unsubstituted aryloxy group having 6–10 carbon atoms, a substituted or unsubstituted acylamino group having 2–10 carbon atoms, a substituted or unsubstituted aminocarbonylamino group having 2–10 carbon atoms, a substituted or unsubstituted alkoxycarbonylamino group having 2–10 carbon atoms, a substituted or unsubstituted aryloxycarbonylamino group having 6–10 carbon atoms, a substituted or unsubstituted sulfamoyl group having 0–10 carbon atoms, a substituted or unsubstituted alkylsulfonyl group having 1–10 carbon atoms, a substituted or unsubstituted arylsulfonyl group having 6–10 carbon atoms, a substituted or unsubstituted acyl group having 2–10 carbon atoms, a substituted or unsubstituted aryloxycarbonyl group having 7–10 carbon atoms, a substituted or unsubstituted alkoxycarbonyl group having 2–10 carbon atoms, or a substituted or unsubstituted carbamoyl group having 1–10 carbon atoms; provided that substituents $R^1$ and $R^2$ may be bonded to each other to form a ring (preferably a 6-membered ring, e.g., cyclohexane).

(3) A Process for Producing a Compound Represented by Formula (I) which comprises reacting a compound represented by the following formula (III) with a compound represented by the following formula (IV):

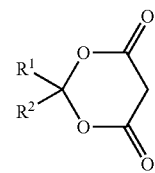

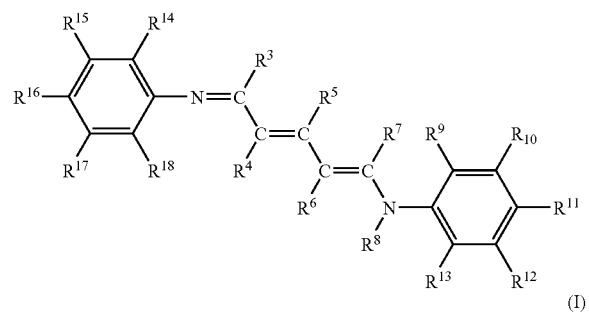

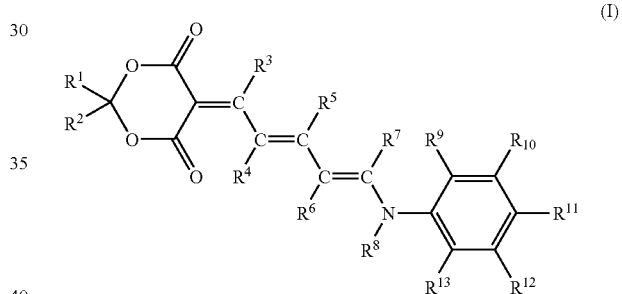

wherein $R^1$ and $R^2$ each independently represent a hydrogen atom, a substituted or unsubstituted alkyl group having 1–10 carbon atoms, or a substituted or unsubstituted aryl group having 6–10 carbon atoms; $R^3$, $R^4$, $R^6$, and $R^7$ each independently represent a hydrogen atom or a substituted or unsubstituted alkyl group having 1–10 carbon atoms; $R^5$ represents a hydrogen atom, a halogen atom, a substituted or unsubstituted alkyl group having 1–10 carbon atoms, a substituted or unsubstituted aryl group having 6–10 carbon atoms, a substituted or unsubstituted acylamino group having 2–10 carbon atoms, or a substituted or unsubstituted heterocyclic group having 1–6 carbon atoms; $R^8$ represents a hydrogen atom or a substituted or unsubstituted acyl group having 2–10 carbon atoms; and $R^9$, $R^{10}$, $R^{11}$, $R^{12}$, $R^{13}$, $R^{14}$, $R^{15}$, $R^{16}$, $R^{17}$, and $R^{18}$ each independently represent a hydrogen atom or a substituent; provided that substituents $R^1$ and $R^2$ may be bonded to each other to form a ring (preferably a 6-membered ring, e.g., cyclohexane).

The compound of the invention is a completely novel compound, and an oxonol dye showing excellent performances when used in DVD-R's can be easily synthesized therefrom in a satisfactory yield. Since the starting materials used are easily available and inexpensive, the compound of the invention is a preferred intermediate from the standpoint of industrial production.

BEST MODE FOR CARRYING OUT THE INVENTION

The invention is explained in detail.

In the formulae, $R^1$ and $R^2$ each independently represent a hydrogen atom, a substituted or unsubstituted alkyl group having 1–10 carbon atoms, or a substituted or unsubstituted aryl group having 6–10 carbon atoms. Substituents $R^1$ and $R^2$ may be bonded to each other to form a ring (preferably a 5- or 6-membered ring, e.g., cyclohexane).

When $R^1$ or $R^2$ is substituted by one or more substituents, examples of the substituents include halogen atoms, alkyl groups (including cycloalkyl groups and bicycloalkyl groups), alkenyl groups (including cycloalkenyl groups and bicycloalkenyl groups), alkynyl groups, aryl groups, heterocyclic groups, cyano, hydroxyl, nitro, carboxyl, alkoxy groups, aryloxy groups, silyloxy groups, heterocycle-oxy groups, acyloxy groups, carbamoyloxy groups, alkoxycarbonyloxy groups, aryloxycarbonyloxy groups, amino groups (including anilino), acylamino groups, aminocarbonylamino groups, alkoxycarbonylamino groups, aryloxycarbonylamino groups, sulfamoylamino groups, alkyl- and arylsulfonylamino groups, mercapto, alkylthio groups, arylthio groups, heterocycle-thio groups, sulfamoyl groups, sulfo, alkyl- and arylsulfinyl groups, alkyl- and arylsulfonyl groups, acyl groups, aryloxycarbonyl groups, alkoxycarbonyl groups, carbamoyl groups, aryl- and heterocycle-azo groups, imide groups, phosphino groups, phosphinyl groups, phosphinyloxy groups, phosphinylamino groups, and silyl groups.

More specifically, the substituents include halogen atoms (e.g., chlorine, bromine, and iodine atoms), alkyl groups [i.e., linear, branched, or cyclic, substituted or unsubstituted alkyl groups, which include alkyl groups (preferably, alkyl groups having 1–10 carbon atoms, e.g., methyl, ethyl, n-propyl, isopropyl, t-butyl, n-octyl, eicosyl, 2-chloroethyl, 2-cyanoethyl, and 2-ethylhexyl), cycloalkyl groups (preferably, substituted or unsubstituted cycloalkyl groups having 3–30 carbon atoms, e.g., cyclohexyl, cyclopentyl, and 4-n-dodecylcyclohexyl), bicycloalkyl groups (preferably, substituted or unsubstituted bicycloalkyl groups having 5–30 carbon atoms, i.e., monovalent groups formed by removing one hydrogen atom from bicycloalkanes having 5–30 carbon atoms; examples thereof include bicyclo [1.2.2]hept-2-yl and bicyclo[2.2.2]oct-3-yl), and alkyl groups made up of a larger number of cycles, such as tricyclic structures; alkyl groups in substituents explained below (e.g., the alkyl groups in the alkylthio groups) also are alkyl groups having the same conception], alkenyl groups [i.e., linear, branched, or cyclic, substituted or unsubstituted alkenyl groups, which include alkenyl groups (preferably, substituted or unsubstituted alkenyl groups having 2–30 carbon atoms, e.g., vinyl, allyl, prenyl, geranyl, and oleyl), cycloalkenyl groups (preferably, substituted or unsubstituted cycloalkenyl groups having 3–30 carbon atoms, i.e., monovalent groups formed by removing one hydrogen atom from cycloalkenes having 3–30 carbon atoms; examples thereof include 2-cyclopenten-1-yl and 2-cyclohexen-1-yl), and bicycloalkenyl groups (substituted or unsubstituted bicyclo alkenyl groups, preferably substituted or unsubstituted bicyclo alkenyl groups having 5–30 carbon atoms, i.e., monovalent groups formed by removing one hydrogen atom from bicyclo alkenes, which have one double bond; examples thereof include bicyclo [2.2.1]hept-2-en-1-yl and bicyclo[2.2.2]oct-2-en-4-yl)], alkynyl groups (preferably, substituted or unsubstituted alkynyl groups having 2–30 carbon atoms, such as, e.g., ethynyl, propargyl, and trimethylsilylethynyl), aryl groups (preferably, substituted or unsubstituted aryl groups having 6–30 carbon atoms, such as, e.g., phenyl, p-tolyl, naphthyl, m-chlorophenyl, and o-hexadecanoylaminophenyl), heterocyclic groups (preferably, monovalent groups formed by removing one hydrogen atom from 5- or 6-membered, substituted or unsubstituted, aromatic or non-aromatic heterocyclic compounds, more preferably, 5- or 6-membered aromatic heterocyclic groups having 3–30 carbon atoms; examples thereof include 2-furyl, 2-thienyl, 2-pyrimidinyl, and 2-benzothiazolyl), cyano, hydroxyl, nitro, carboxyl, alkoxy groups (preferably, substituted or unsubstituted alkoxy groups having 1–30 carbon atoms, such as, e.g., methoxy, ethoxy, isopropoxy, t-butoxy, n-octyloxy, and 2-methoxyethoxy), aryloxy groups (preferably, substituted or unsubstituted aryloxy groups having 6–30 carbon atoms, such as, e.g., phenoxy, 2-methylphenoxy, 4-t-butylphenoxy, 3-nitrophenoxy, and 2-tetradecanoylaminophenoxy), silyloxy groups (preferably, silyloxy groups having 3–20 carbon atoms, such as, e.g., trimethylsilyloxy and t-butyldimethylsilyloxy), heterocycle-oxy groups (preferably, substituted or unsubstituted heterocycle-oxy groups having 2–30 carbon atoms, such as, e.g., 1-phenyltetrazolyl-5-oxy and 2-tetrahydropyranyloxy), acyloxy groups (preferably, formyloxy, and substituted or unsubstituted alkyl carbonyloxy groups having 2–30 carbon atoms and substituted or unsubstituted arylcarbonyloxy groups having 6–30 carbon atoms, such as, e.g., acetyloxy, pivaloyloxy, stearyloxy, benzoyloxy, and p-methoxyphenylcarbonyloxy), carbamoyloxygroups (preferably, substituted or unsubstituted carbamoyloxy groups having 1–30 carbon atoms, such as, e.g., N,N-dimethylcarbamoyloxy, N,N-diethylcarbamoyloxy, morpholinocarbonyloxy, N,N-di-n-octylaminocarbonyloxy, and N-n-octylcarbamoyloxy), alkoxycarbonyloxy groups (preferably, substituted or unsubstituted alkoxycarbonyloxy groups having 2–30 carbon atoms, such as, e.g., methoxycarbonyloxy, ethoxycarbonyloxy, t-butoxycarbonyloxy, and n-octylcarbonyloxy), aryloxycarbonyloxy groups (preferably, substituted or unsubstituted aryloxycarbonyloxy groups having 7–30 carbon atoms, such as, e.g., phenoxycarbonyloxy, p-methoxyphenoxycarbonyloxy, and p-n-hexadecyloxyphenoxycarbonyloxy), amino groups (preferably, amino, and substituted or unsubstituted alkyl amino groups having 1–30 carbon atoms and substituted or unsubstituted arylamino groups having 6–30 carbon atoms, such as, e.g., methylamino, dimethylamino, anilino, N-methylanilino, and diphenylamino), acylamino groups (preferably, substituted or unsubstituted alkylcarbonylamino groups having 1–30 carbon atoms and substituted or unsubstituted arylcarbonylamino groups having 6–30 carbon atoms, such as, e.g., formylamino, acetylamino, pivaloylamino, lauroylamino, benzoylamino, and 3,4,5-tri-n-octyloxyphenylcarbonylamino), aminocarbonylamino groups (preferably, substituted or unsubstituted aminocarbonylamino groups having 1–30 carbon atoms, such as, e.g., carbamoylamino, N,N-dimethylaminocarbonylamino, N,N-diethylaminocarbonylamino, and morpholinocarbonylamino), alkoxycarbonylamino groups (preferably, substituted or unsubstituted alkoxycarbonylamino groups having 2–30 carbon atoms, such as, e.g., methoxycarbonylamino, ethoxycarbonylamino, t-butoxycarbonylamino, n-octadecyloxycarbonylamino, and N-methylmethoxycarbonylamino), aryloxycarbonylamino groups (preferably, substituted or unsubstituted aryloxycarbonylamino groups having 7–30 carbon atoms, such as, e.g., phenoxycarbonylamino, p-chlorophenoxycarbonylamino, and m-n-octyloxyphenoxycarbonylamino), sulfamoylamino groups (preferably, substituted or unsubstituted sulfamoylamino groups having 0–30 carbon atoms, such as, e.g., sulfamoylamino, N,N-dimethylaminosulfonylamino, and N-n-octylaminosulfonylamino), alkyl- and arylsulfonylamino groups (preferably, substituted or unsubstituted alkylsulfonylamino groups having 1–30 carbon atoms and substituted or unsubstituted arylsulfonylamino groups having 6–30 carbon atoms, such as, e.g., methylsulfonylamino, butylsulfonylamino, phenylsulfonylamino, 2,3,5-trichlorophenylsulfonylamino, and p-methylphenylsulfonylamino), mercapto, alkylthio groups (preferably, substituted or unsubstituted alkylthio groups having 1–30 carbon atoms, such as, e.g., methylthio, ethylthio, and n-hexadecylthio), arylthiogroups (preferably, substituted or unsubstituted arylthio groups having 6–30 carbon atoms, such as, e.g., phenylthio, p-chlorophenylthio, and m-methoxyphenylthio), heterocycle-thio groups (preferably, substituted or unsubstituted heterocycle-thio groups having 2–30 carbon atoms, such as, e.g., 2-benzothiazolylthio and 1-phenyltetrazol-5-yl thio), sulfamoyl groups (preferably, substituted or unsubstituted sulfamoyl groups having 0–30 carbon atoms, such as, e.g., N-ethylsulfamoyl, N-(3-dodecyloxypropyl)sulfamoyl, N,N-dimethylsulfamoyl, N-acetylsulfamoyl, N-benzoylsulfamoyl, and N-(N'-phenylcarbamoyl)sulfamoyl), sulfo, alkyl- and arylsulfinyl groups (preferably, substituted or unsubstituted alkylsulfinyl groups having 1–30 carbon atoms and substituted or unsubstituted arylsulfinyl groups having 6–30 carbon atoms, such as, e.g., methylsulfinyl, ethylsulfinyl, phenylsulfinyl, and p-methylphenylsulfinyl), alkyl- and arylsulfonyl groups (preferably, substituted or unsubstituted alkylsulfonyl groups having 1–30 carbon atoms and substituted or unsubstituted arylsulfonyl groups having 6–30 carbon atoms, such as, e.g., methylsulfonyl, ethylsulfonyl, phenylsulfonyl, and p-methylphenylsulfonyl), acyl groups (preferably, formyl, and substituted or unsubstituted alkylcarbonyl groups having 2–30 carbon atoms, substituted or unsubstituted arylcarbonyl groups having 7–30 carbon atoms, and substituted or unsubstituted heterocycle-carbonyl groups which have 4–30 carbon atoms and in which the heterocycle is bonded through a carbon atom thereof to the carbonyl group, such as, e.g., acetyl, pivaloyl, 2-chloroacetyl, stearoyl, benzoyl, p-n-octyloxyphenylcarbonyl, 2-pyridylcarbonyl, and 2-furylcarbonyl), aryloxycarbonyl groups (preferably, substituted or unsubstituted aryloxycarbonyl groups having 7–30 carbon atoms, such as, e.g., phenoxycarbonyl, o-chlorophenoxycarbonyl, m-nitrophenoxycarbonyl, and p-t-butylphenoxycarbonyl), alkoxycarbonyl groups (preferably, substituted or unsubstituted alkoxycarbonyl groups having 2–30 carbon atoms, such as, e.g., methoxycarbonyl, ethoxycarbonyl, t-butoxycarbonyl, and n-octadecyloxycarbonyl), carbamoyl groups (preferably, substituted or unsubstituted carbamoyl groups having 1–30 carbon atoms, such as, e.g., carbamoyl, N-methylcarbamoyl, N,N-dimethylcarbamoyl, N,N-di-n-octylcarbamoyl, and N-(methylsulfonyl)carbamoyl), aryl- and heterocycle-azo groups (preferably, substituted or unsubstituted arylazo groups having 6–30 carbon atoms and substituted or unsubstituted heterocycle-azo groups having 3–30 carbon atoms, such as, e.g., phenylazo, p-chlorophenylazo, and 5-ethylthio-1,3,4-thiadiazol-2-ylazo), imide groups (preferably, N-succinimido and N-phthalimido), phosphino groups (preferably, substituted or unsubstituted phosphino groups having 2–30 carbon atoms, such as, e.g., dimethylphosphino, diphenylphosphino, and methylphenoxyphosphino), phosphinyl groups (preferably, substituted or unsubstituted phosphinyl groups having 2–30 carbon atoms, such as, e.g., phosphinyl, dioctyloxyphosphinyl, and diethoxyphosphinyl), phosphinyloxy groups (preferably, substituted or unsubstituted phosphinyloxy groups having 2–30 carbon atoms, such as, e.g., diphenoxyphosphinyloxy and dioctyloxyphosphinyloxy), phosphinylamino groups (preferably, substituted or unsubstituted phosphinylamino groups having 2–30 carbon atoms, such as, e.g., dimethoxyphosphinylamino and dimethylaminophosphinylamino), and silyl groups (preferably, substituted or unsubstituted silyl groups having 3–30 carbon atoms, such as, e.g., trimethylsilyl, t-butyldimethylsilyl, and phenyldimethylsilyl).

Of the functional groups shown above, those which have one or more hydrogen atoms may be ones in which one or more of the hydrogen atoms have been replaced by any of the groups shown above. Examples of these functional groups include alkylcarbonylaminosulfonyl groups, arylcarbonylaminosulfonyl groups, alkylsulfonylaminocarbonyl groups, and arylsulfonylaminocarbonyl groups. Specific examples thereof include methylsulfonylaminocarbonyl, p-methylphenylsulfonylaminocarbonyl, acetylaminosulfonyl, and benzoylaminosulfonyl.

Preferably, $R^1$ and $R^2$ each independently are a substituted or unsubstituted alkyl group having 1–10 carbon atoms or represent a cyclohexane ring (formed by the bonding of substituents $R^1$ and $R^2$ to each other). More preferably, $R^1$ and $R^2$ are different and each are an alkyl group having 1–10 carbon atoms which is unsubstituted or has been substituted by an alkoxycarbonyl group having 1–5 carbon atoms, acyloxy group having 1–5 carbon atoms, or alkoxy group having 1–5 carbon atoms, or $R^1$ and $R^2$ form a cyclohexane ring.

$R^3$, $R^4$, $R^6$, and $R^7$ each independently represent a hydrogen atom or a substituted or unsubstituted alkyl group having 1–10 carbon atoms. Preferably, $R^3$, $R^4$, $R^6$, and $R^7$ each are a hydrogen atom.

$R^5$ represents a hydrogen atom, a halogen atom, a substituted or unsubstituted alkyl group having 1–10 carbon atoms, a substituted or unsubstituted aryl group having 6–10 carbon atoms, a substituted or unsubstituted acylamino group having 2–10 carbon atoms, or a substituted or unsubstituted heterocyclic group having 1–6 carbon atoms. Preferably, $R^5$ is a hydrogen atom, an unsubstituted alkyl group having 1–5 carbon atoms, or an unsubstituted aryl group having 6–10 carbon atoms. Most preferably, $R^5$ is a hydrogen atom.

$R^8$ represents a hydrogen atom or a substituted or unsubstituted acyl group having 2–10 carbon atoms. Preferably, $R^8$ is a hydrogen atom.

Examples of $R^5$ include the corresponding ones among the substituents shown above with regard to substituents for $R^1$ and $R^2$.

$R^9$, $R^{10}$, $R^{11}$, $R^{12}$, and $R^{13}$ each independently represent a hydrogen atom or a substituent. Examples of the substituent include the substituents shown above with regard to substituents for $R^1$ and $R^2$. Preferably, $R^9$, $R^{10}$, $R^{11}$, $R^{12}$, and $R^{13}$ each are a hydrogen atom, a halogen atom, a substituted or unsubstituted alkyl group having 1–10 carbon atoms, nitro, cyano, a substituted or unsubstituted alkoxycarbonylamino group having 2–10 carbon atoms, a substituted or unsubstituted alkoxy group having 1–10 carbon atoms, or a substituted or unsubstituted alkoxycarbonyl group having 2–10 carbon atoms. More preferably, $R^9$ to $R^{13}$ each are a hydrogen atom, a halogen atom, nitro, or an alkyl group having 1–5 carbon atoms which is unsubstituted or has been substituted by one or more halogen atoms. Especially preferably, $R^9$ to $R^{13}$ each are a hydrogen atom.

The compound represented by formula (I) preferably has a structure represented by formula (II). In formula (II), $R^1$ and $R^2$ each independently represent a hydrogen atom, a substituted or unsubstituted alkyl group having 1–10 carbon atoms, or a substituted or unsubstituted aryl group having 6–10 carbon atoms; $R^5$ represents a hydrogen atom, a halogen atom, a substituted or unsubstituted alkyl group having 1–10 carbon atoms, a substituted or unsubstituted aryl group having 6–10 carbon atoms, a substituted or unsubstituted acylamino group having 2–10 carbon atoms, or a substituted or unsubstituted heterocyclic group having 1–6 carbon atoms; and $R^9$, $R^{10}$, $R^{11}$, $R^{12}$, and $R^{13}$ each independently represent a hydrogen atom, a halogen atom, an alkyl group, a cyano group, a nitro group, a carboxyl group, a substituted or unsubstituted alkoxy group having 1–10 carbon atoms, a substituted or unsubstituted aryloxy group having 6–10 carbon atoms, a substituted or unsubstituted acylamino group having 2–10 carbon atoms, a substituted or unsubstituted amino carbonylamino group having 2–10 carbon atoms, a substituted or unsubstituted alkoxycarbonylamino group having 2–10 carbon atoms, a substituted or unsubstituted aryloxycarbonylamino group having 6–10 carbon atoms, a substituted or unsubstituted sulfamoyl group having 0–10 carbon atoms, a substituted or unsubstituted alkyl sulfonyl group having 1–10 carbon atoms, a substituted or unsubstituted arylsulfonyl group having 6–10 carbon atoms, a substituted or unsubstituted acyl group having 2–10 carbon atoms, a substituted or unsubstituted aryloxycarbonyl group having 7–10 carbon atoms, a substituted or unsubstituted alkoxycarbonyl group having 2–10 carbon atoms, or a substituted or unsubstituted carbamoyl group having 1–10 carbon atoms.

The structure represented by formula (II) preferably is as follows. $R^1$ and $R^2$ are different and each are an alkyl group having 1–10 carbon atoms which is unsubstituted or has been substituted by an alkoxycarbonyl group having 1–5 carbon atoms, acyloxy group having 1–5 carbon atoms, or alkoxy group having 1–5 carbon atoms, or $R^1$ and $R^2$ represent a cyclohexane ring (formed by the bonding of substituents $R^1$ and $R^2$ to each other). $R^5$ is a hydrogen atom, an unsubstituted alkyl group having 1–5 carbon atoms, or an unsubstituted aryl group having 6–10 carbon atoms, and preferably is a hydrogen atom. $R^9$, $R^{10}$, $R^{11}$, $R^{12}$, and $R^{13}$ each independently are a hydrogen atom, a halogen atom, nitro, or an alkyl group having 1–5 carbon atoms which is unsubstituted or has been substituted by one or more halogen atoms. It is preferred that one of $R^{10}$, $R^{11}$, and $R^{12}$ be a hydrogen atom, alkyl group, halogen atom, nitro, alkoxy group, acylamino group, or carbamoyl group and $R^9$ and $R^{13}$ each be a hydrogen atom. More preferably, $R^9$, $R^{10}$, $R^{11}$, $R^{12}$, and $R^{13}$ each are a hydrogen atom.

The compound represented by formula (I) of the invention is a novel compound synthesized first by the present inventors.

A process (synthesis method) for producing the compound represented by formula (I) is explained below.

The compound represented by formula (I) is synthesized by reacting a compound represented by the following formula (III) with a compound represented by the following formula (IV).

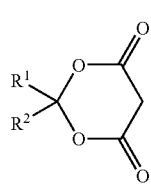

(III)

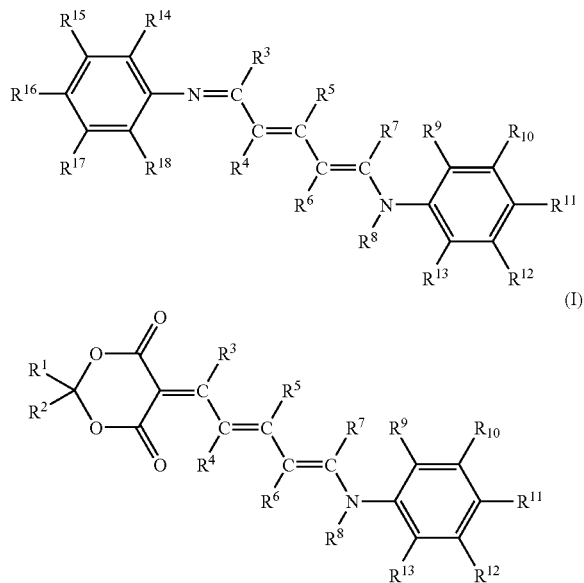

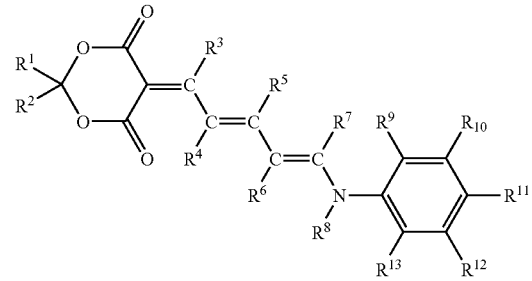

In the formulae, $R^1$ and $R^2$ each independently represent a hydrogen atom, a substituted or unsubstituted alkyl group having 1–10 carbon atoms, or a substituted or unsubstituted aryl group having 6–10 carbon atoms; $R^3$, $R^4$, $R^6$, and $R^7$ each independently represent a hydrogen atom or a substituted or unsubstituted alkyl group having 1–10 carbon atoms; $R^5$ represents a hydrogen atom, a halogen atom, a substituted or unsubstituted alkyl group having 1–10 carbon atoms, a substituted or unsubstituted aryl group having 6–10 carbon atoms, a substituted or unsubstituted acylamino group having 2–10 carbon atoms, or a substituted or unsubstituted heterocyclic group having 1–6 carbon atoms; $R^8$ represents a hydrogen atom or a substituted or unsubstituted acyl group having 2–10 carbon atoms; and $R^9$, $R^{10}$, $R^{11}$, $R^{12}$, $R^{13}$, $R^{14}$, $R^{15}$, $R^{16}$, $R^{17}$, and $R^{18}$ each independently represent a hydrogen atom or a substituent.

For the reaction, any solvent may be used. Examples thereof include alcohols (e.g., methanol, ethanol, and isopropanol), amides (e.g., dimethylformamide and dimethylacetamide), aromatic hydrocarbons (e.g., toluene and xylene), halogenated hydrocarbons (e.g., chloroform, methylene chloride, and dichloroethane), and hydrocarbons (e.g., hexane and pentane).

A temperature can be selected from the range of from –20° C. to 200° C. However, the temperature is preferably –10° C. to 100° C., more preferably 0–50° C., most preferably 10–40° C.

The reaction time varies depending on the conditions including temperature. However, it is preferably from 5 minutes to 10 hours.

It is preferred that a base be caused to coexist in the reaction system. Examples of the base include inorganic bases (e.g., sodium carbonate, sodium hydrogen carbonate, potassium carbonate, sodium hydroxide, and potassium hydroxide) and organic bases (e.g., triethylamine, pyridine, and diazabicycloundecene). The base preferably is an organic base.

The compound (III) and compound (IV) are used preferably in a proportion (molar ratio) selected from the range of from 1:10 to 10:1 in terms of equivalent ratio. The proportion thereof is more preferably from 1:3 to 3:1, most preferably from 1:1.5 to 1.5:1.
Preferred examples of the compound represented by formula (I) of the invention are shown below, but the compound of the invention should not be construed as being limited to the following examples.
1.
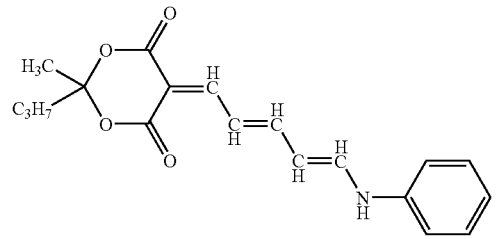
2.
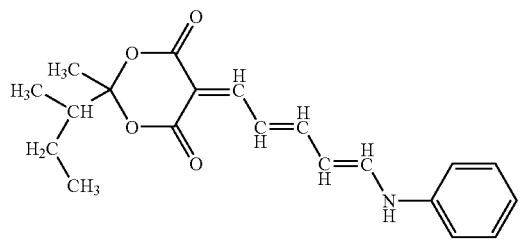
3.
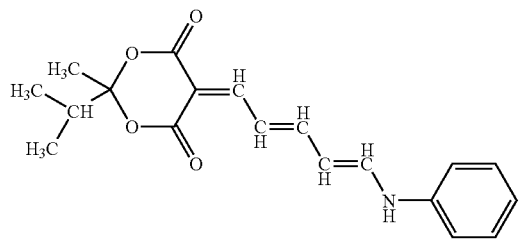
4.
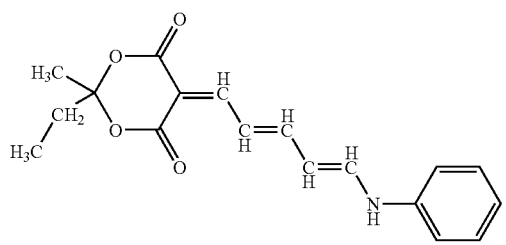
5.
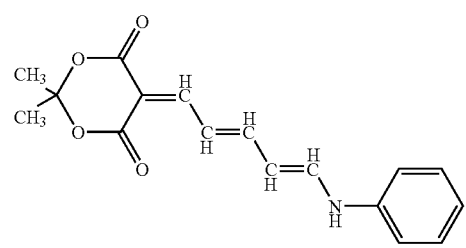
6.
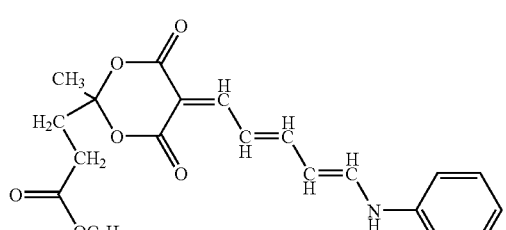
-continued
7.
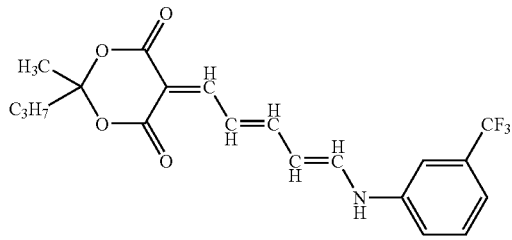
8.
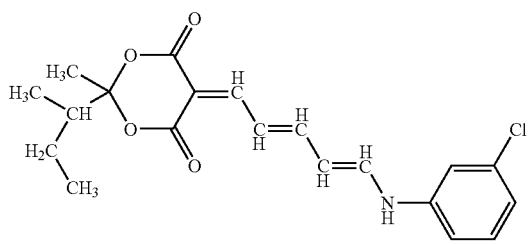
9.
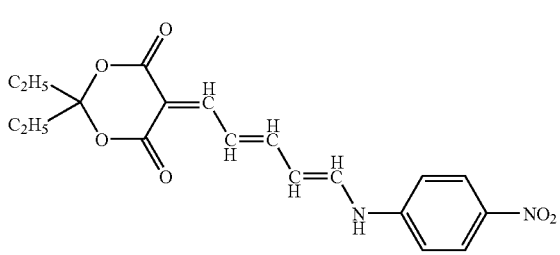
10.
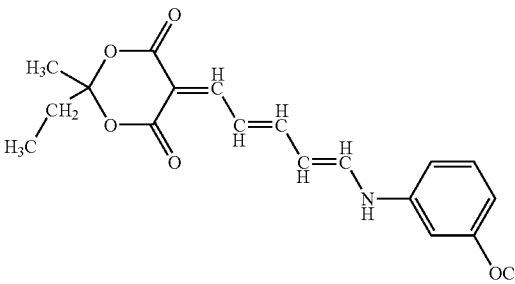
11.
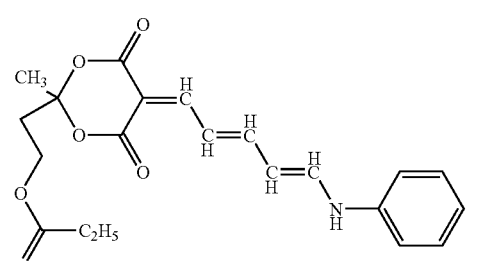
12.
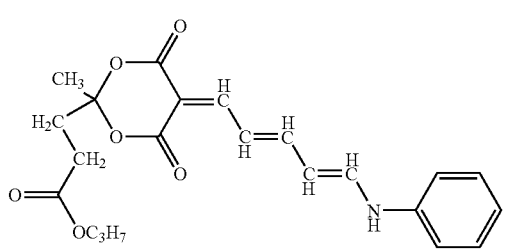

13.

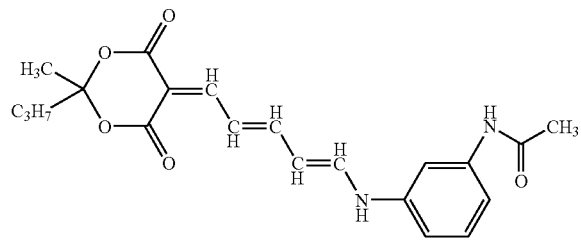

14.

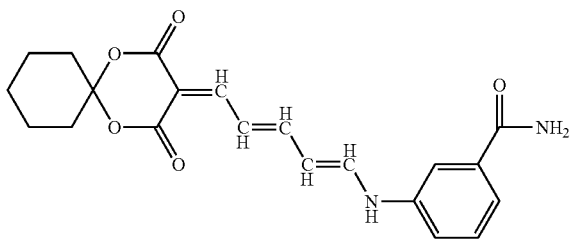

15.

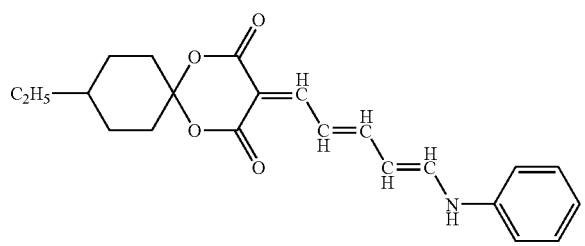

16.

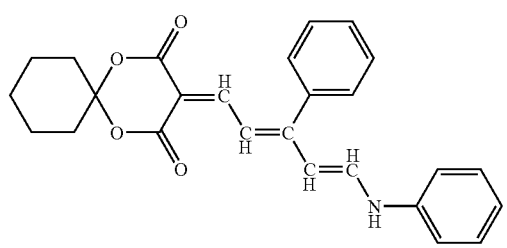

17.

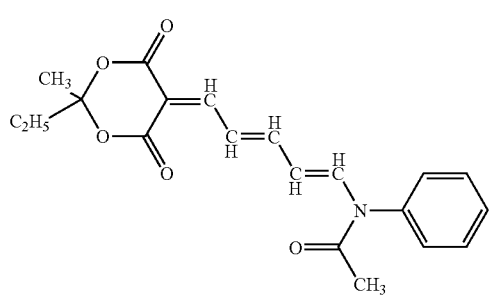

18.

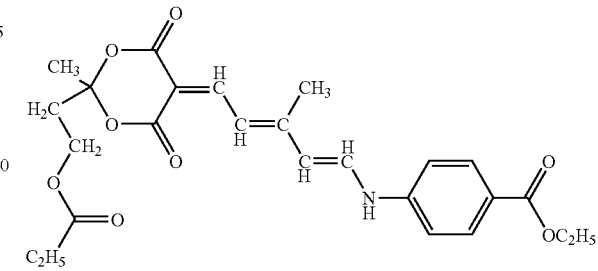

The method for synthesizing the compound of the invention is explained. The compound of the invention can be synthesized via the following synthesis route.

(Synthesis Route)

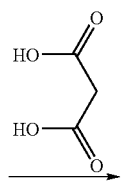

Intermediate A

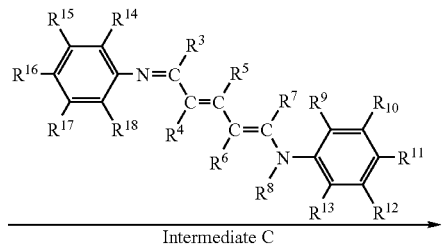

Intermediate B

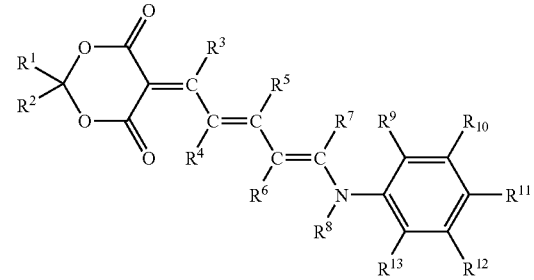

Compound of formula (I)

In the formulae, $R^1$ and $R^2$ each independently represent a hydrogen atom, a substituted or unsubstituted alkyl group having 1–10 carbon atoms, or a substituted or unsubstituted aryl group having 6–10 carbon atoms; $R^3$, $R^4$, $R^6$, and $R^7$ each independently represent a hydrogen atom or a substituted or unsubstituted alkyl group having 1–10 carbon atoms; $R^5$ represents a hydrogen atom, a halogen atom, a substituted or unsubstituted alkyl group having 1–10 carbon atoms, a substituted or unsubstituted aryl group having 6–10 carbon atom, a substituted or unsubstituted acylamino group having 2–10 carbon atoms, or a substituted or unsubstituted heterocyclic group having 1–6 carbon atoms; $R^8$ represents a hydrogen atom or a substituted or unsubstituted acyl group having 2–10 carbon atoms; and $R^9$, $R^{10}$, $R^{11}$, $R^{12}$, $R^{13}$, $R^{14}$, $R^{15}$, $R^{16}$, $R^{17}$, and $R^{18}$ each independently represent a hydrogen atom or a substituent; provided that substituents $R^1$ and $R^2$ may be bonded to each other to form a ring.

EXAMPLES

The invention will be explained below in more detail by reference to Examples.

Example 1

Synthesis of Compound 15

Synthesis Example 1

(Step 1)

Malonic acid (5.2 g, 0.05 mol) and concentrated sulfuric acid (0.5 mL) were added to acetic anhydride (10 mL). This mixture was stirred at room temperature to completely dissolve the starting compounds. Thereafter, 4-ethylcyclohexanone (6.31 g, 0.05 mol) was gradually added dropwise to the solution with cooling on an ice bath. The resultant mixture was continuously stirred on the ice bath. As a result, colorless crystals precipitated as the reaction proceeded. These crystals were taken out by filtration, washed with distilled water, and then dried. Thus, intermediate 1 was obtained as colorless crystals in an amount of 9.0 g (yield, 85.1%).

(Step 2)

The intermediate 1 (4.25 g, 0.02 mol) and intermediate 2 (5.70 g, 0.02 mol) were dissolved in methanol (50 mL), and triethylamine (3.04 g, 0. 03 mol) was added thereto. This mixture was continuously stirred at room temperature for 6 hours. As a result, purple crystals precipitated. These crystals were taken out by filtration and washed with methanol. Thus, compound 15 was obtained as purple crystals in an amount of 5.61 g (yield, 76.3%).

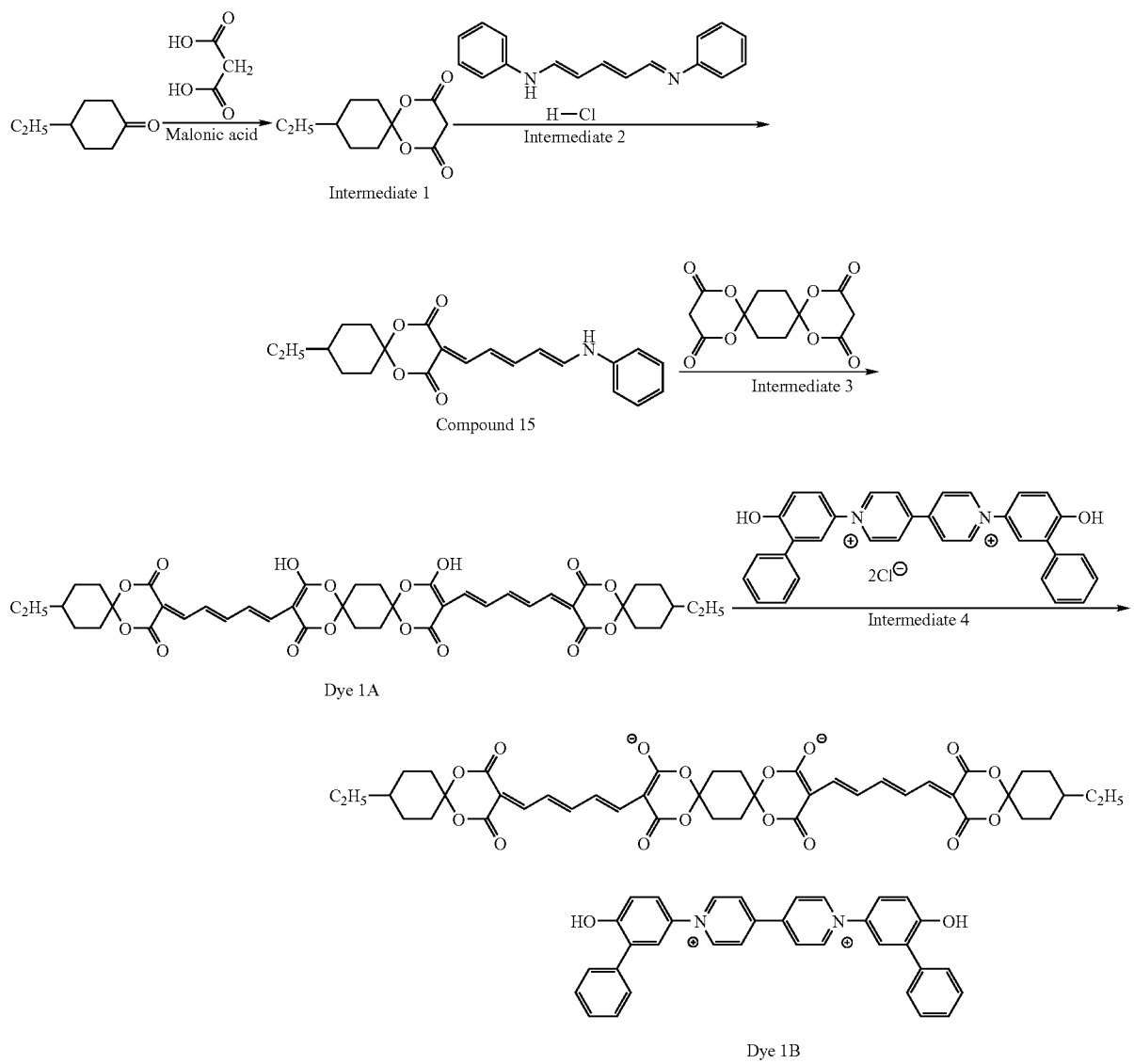

Reference Example

That the compound of the invention is useful as a starting material for synthesizing an oxonol dye showing excellent performances in DVD-R's is demonstrated by a Synthesis Example.

Synthesis of Intermediate 3

1,4-Cyclohexadione (22.43 g, 0.2 mol) and malonic acid (41.62 g, 0.4 mol) were dissolved in acetic anhydride (85 mL), and concentrated sulfuric acid (7.0 mL, 0.12 mol) was added thereto. This mixture was stirred on an ice bath. Light-brown crystals precipitated as the reaction proceeded. These crystals were taken out by filtration, washed with ice-cooled distilled water, and then dried. Thus, intermediate 3 was obtained as light-brown crystals in an amount of 8.8 g (yield, 15.5%).

(Step 3)

The compound 15 (4.40 g, 12.0 mmol) according to the invention and the intermediate 3 (1.71 g, 6.0 mmol) shown in the Synthesis Example given above were dissolved in dimethylformamide (20 mL). Triethylamine (1.82 g, 18 mmol) was added dropwise to the solution and this reaction mixture was stirred at 50° C. for 4 hours. Thereafter, distilled water was added to the reaction mixture, and the resultant mixture was extracted with ethyl acetate. The organic layer obtained as an extract was subjected to purification by silica gel column chromatography (dichloromethane/methanol=6/1). Thus, dye 1A was obtained as a purple powder in an amount of 2.0 g (yield, 39.5%).

(Step 4)

The dye 1A (1.24 g, 1.48 mmol) was dissolved in dimethylformamide used in a minimum amount necessary for dissolving the dye. Intermediate 4 serving as a countercation ingredient was added to the solution, and the resultant mixture was continuously stirred at room temperature. As a result, a gold powder precipitated. This powder was taken out by filtration. Thus, dye 1B was obtained as a gold powder in an amount of 0.95 g (yield, 48.3%).

The structure of the dye 1B was ascertained by $^1$H NMR spectroscopy.

$^1$H NMR (DMSO-d6): 0.84 (t, 6H), 1.20 (m, 10H), 1.62 (m, 8H), 1.96–2.14 (m, 12H), 7.11 (m, 4H), 7.24 (d, 2H), 7.34–7.77 (m, 18H), 7.90 (d, 2H), 9.00 (d, 4H), 9.65 (d, 4H), 10.71 (s, 2H)

Example 2

Synthesis of Compound 1

Synthesis Example 2

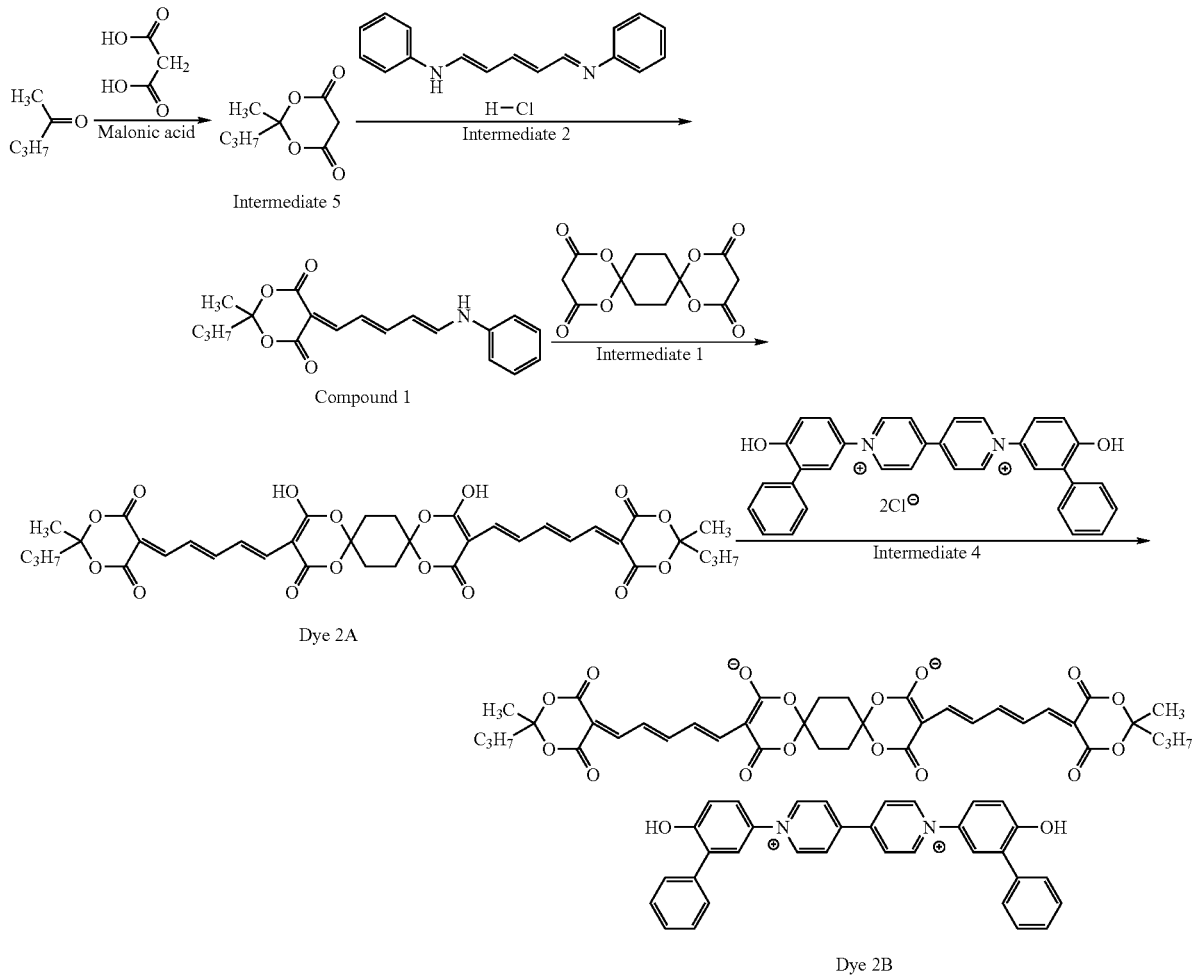

(Step 1)

Malonic acid (5.2 g, 50 mmol) and concentrated sulfuric acid (0.5 mL) were added to acetic anhydride (10 mL). This mixture was stirred at room temperature to completely dissolve the starting compounds. Thereafter, 2-pentanone (4.3 g, 50 mmol) was gradually added dropwise to the solution with cooling on an ice bath. The resultant mixture was continuously stirred at room temperature for 4 hours. The resultant reaction mixture was extracted with ethyl acetate, and the extract was washed with water twice, dehydrated, and then treated with an evaporator to distill off the solvent under reduced pressure. Thus, intermediate 5 was obtained as an oily matter in an amount of 7.15 g (yield, 83%; 41.4 mmol).

(Step 2)

The intermediate 5 (3.44 g, 20 mmol) and intermediate 2 (5.7 g, 20 mmol) were dissolved in methanol (50 mL), and triethylamine (3.04 g, 0.03 mol) was added thereto. This mixture was continuously stirred at room temperature for 4 hours. As a result, purple crystals precipitated. These crystals were taken out by filtration and washed with methanol. Thus, compound 1 was obtained as purple crystals in an amount of 5.3 g (yield, 81.1%; 16.2 mmol).

The compound 1 according to the invention was used to synthesize dye 2B in the same manner as in Example 1. The structure of this dye was determined by NMR spectroscopy.

$^1$H NMR (DMSO-d6): 0.90 (t, 6H), 1.39 (m, 4H), 1.45 (s, 6H), 1.77 (m, 4H), 1.98 (s, 8H), 7.10 (q, 4H), 7.27 (d, 2H), 7.40–7.80 (m, 18H), 7.91 (s, 2H), 9.05 (d, 4H), 9.65 (d, 4H), 10.72 (s, 2H)

This application is based on Japanese Patent application JP 2004-158997, filed May 28, 2004, the entire content of which is hereby incorporated by reference, the same as if set forth at length.

The invention claimed is:

1. A compound represented by the following formula

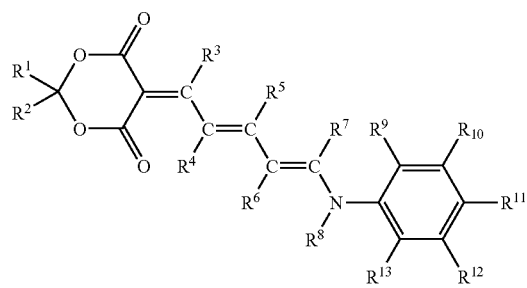

(I)

wherein $R^1$ and $R^2$ each independently represent a hydrogen atom, a substituted or unsubstituted alkyl group having 1 to 10 carbon atoms, or a substituted or unsubstituted aryl group having 6 to 10 carbon atoms; $R^3$, $R^4$, $R^6$, and $R^7$ each independently represent a hydrogen atom or a substituted or unsubstituted alkyl group having 1 to 10 carbon atoms; $R^5$ represents a hydrogen atom, a halogen atom, a substituted or unsubstituted alkyl group having 1 to 10 carbon atoms, a substituted or unsubstituted aryl group having 6 to 10 carbon atoms, a substituted or unsubstituted acylamino group having 2 to 10 carbon atoms, or a substituted or unsubstituted heterocyclic group having 1 to 6 carbon atoms; $R^8$ represents a hydrogen atom or a substituted or unsubstituted acyl group having 2 to 10 carbon atoms; and $R^9$, $R^{10}$, $R^{11}$, $R^{12}$, and $R^{13}$ each independently represent a hydrogen atom or a substituent; provided that $R^1$ and $R^2$ may be bonded to each other to form a ring.

2. The compound according to claim 1, wherein $R^9$, $R^{10}$, $R^{11}$, $R^{12}$, and $R^{13}$ each independently represent a hydrogen atom, a halogen atom, a substituted or unsubstituted alkyl group having 1 to 10 carbon atoms, a nitro group, a cyano group, a substituted or unsubstituted alkoxycarbonylamino group having 2 to 10 carbon atoms, a substituted or unsubstituted alkoxy group having 1 to 10 carbon atoms, or a substituted or unsubstituted alkoxycarbonyl group having 2 to 10 carbon atoms.

3. The compound according to claim 1, which is represented by the following formula (II):

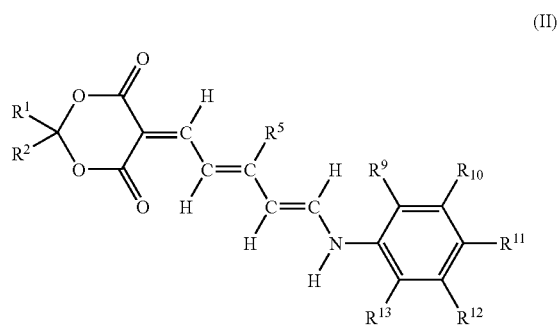

(II)

wherein $R^1$ and $R^2$ each independently represent a hydrogen atom, a substituted or unsubstituted alkyl group having 1 to 10 carbon atoms, or a substituted or unsubstituted aryl group having 6 to 10 carbon atoms; $R^5$ represents a hydrogen atom, a halogen atom, a substituted or unsubstituted alkyl group having 1 to 10 carbon atoms, a substituted or unsubstituted aryl group having 6 to 10 carbon atoms, a substituted or unsubstituted acylamino group having 2 to 10 carbon atoms, or a substituted or unsubstituted heterocyclic group having 1 to 6 carbon atoms; and $R^9$, $R^{10}$, $R^{11}$, $R^{12}$, and $R^{13}$ each independently represent a hydrogen atom, a halogen atom, an alkyl group, a cyano group, a nitro group, a carboxyl group, a substituted or unsubstituted alkoxy group having 1 to 10 carbon atoms, a substituted or unsubstituted aryloxy group having 6 to 10 carbon atoms, a substituted or unsubstituted acylamino group having 2 to 10 carbon atoms, a substituted or unsubstituted aminocarbonylamino group having 2 to 10 carbon atoms, a substituted or unsubstituted alkoxycarbonylamino group having 2 to 10 carbon atoms, a substituted or unsubstituted aryloxycarbonylamino group having 6 to 10 carbon atoms, a substituted or unsubstituted sulfamoyl group having 0 to 10 carbon atoms, a substituted or unsubstituted alkylsulfonyl group having 1 to 10 carbon atoms, a substituted or unsubstituted arylsulfonyl group having 6 to 10 carbon atoms, a substituted or unsubstituted acyl group having 2 to 10 carbon atoms, a substituted or unsubstituted aryloxycarbonyl group having 7 to 10 carbon atoms, a substituted or unsubstituted alkoxycarbonyl group having 2 to 10 carbon atoms, or a substituted or unsubstituted carbamoyl group having 1 to 10 carbon atoms; provided that $R^1$ and $R^2$ may be bonded to each other to form a ring.

4. The compound according to claim 3, wherein $R^5$ represents a hydrogen atom, an unsubstituted alkyl group having 1 to 5 carbon atoms, or an unsubstituted aryl group having 6 to 10 carbon atoms.

5. The compound according to claim 3, wherein $R^5$ represents a hydrogen atom.

6. The compound according to claim 3, wherein $R^9$, $R^{10}$, $R^{11}$, $R^{12}$, and $R^{13}$ each independently represent a hydrogen atom, a halogen atom, a nitro group, or an alkyl group having 1 to 5 carbon atoms which is unsubstituted or is substituted by one or more halogen atoms.

7. The compound according to claim 3, wherein one of $R^{10}$, $R^{11}$, and $R^{12}$ represents a hydrogen atom, an alkyl group, a halogen atom, a nitro group, an alkoxy group, an acylamino group, or a carbamoyl group, and $R^9$ and $R^{13}$ each represent a hydrogen atom.

8. The compound according to claim 3, wherein $R^9$, $R^{10}$, $R^{11}$, $R^{12}$, and $R^{13}$ each represent a hydrogen atom.

9. A process for producing a compound represented by the following formula (I) which comprises reacting a compound represented by the following formula (III) with a compound represented by the following formula (IV):

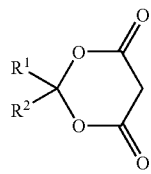
(III)

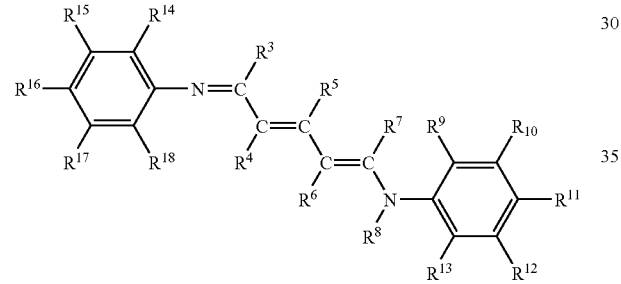
(IV)

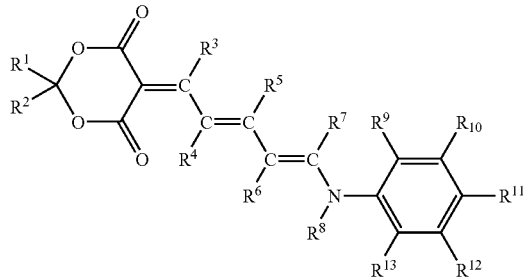
(I)

wherein $R^1$ and $R^2$ each independently represent a hydrogen atom, a substituted or unsubstituted alkyl group having 1 to 10 carbon atoms, or a substituted or unsubstituted aryl group having 6 to 10 carbon atoms; $R^3$, $R^4$, $R^6$, and $R^7$ each independently represent a hydrogen atom or a substituted or unsubstituted alkyl group having 1 to 10 carbon atoms; $R^5$ represents a hydrogen atom, a halogen atom, a substituted or unsubstituted alkyl group having 1 to 10 carbon atoms, a substituted or unsubstituted aryl group having 6 to 10 carbon atoms, a substituted or unsubstituted acylamino group having 2 to 10 carbon atoms, or a substituted or unsubstituted heterocyclic group having 1 to 6 carbon atoms; $R^8$ represents a hydrogen atom or a substituted or unsubstituted acyl group having 2 to 10 carbon atoms; and $R^9$, $R^{10}$, $R^{11}$, $R^{12}$, $R^{13}$, $R^{14}$, $R^{15}$, $R^{16}$, $R^{17}$, and $R^{18}$ each independently represent a hydrogen atom or a substituent; provided that $R^1$ and $R^2$ may be bonded to each other to form a ring.

10. The process according to claim 9, wherein the reacting is made at a temperature of –20° C. to 200° C. for 5 minutes to 10 hours.

* * * * *